United States Patent
Ben-Nun

(10) Patent No.: US 6,846,295 B1
(45) Date of Patent: Jan. 25, 2005

(54) COMPRESSION SLEEVE

(75) Inventor: Asher Ben-Nun, Carmiel (IL)

(73) Assignee: Mego Afek Industrial Measuring Instruments, Doar Afek (IL)

(*) Notice: Subject to any disclaimer, the term of this patent is extended or adjusted under 35 U.S.C. 154(b) by 0 days.

(21) Appl. No.: 09/715,050

(22) Filed: Nov. 20, 2000

(51) Int. Cl.⁷ .................................................. A61H 9/00
(52) U.S. Cl. ................ 601/152; 601/151; 128/DIG. 20
(58) Field of Search .............................. 601/148, 149, 601/150, 151, 152, 15; 606/201; 602/13; 128/DIG. 15, DIG. 20

(56) References Cited

U.S. PATENT DOCUMENTS

| | | | |
|---|---|---|---|
| 3,454,010 A | | 7/1969 | Lilligren et al. |
| 4,013,069 A | | 3/1977 | Hasty |
| 4,338,923 A | * | 7/1982 | Gelfer et al. ............... 601/150 |
| 4,402,312 A | * | 9/1983 | Villari et al. ............... 601/152 |
| 4,762,121 A | | 8/1988 | Shienfeld |
| 5,014,681 A | * | 5/1991 | Neeman et al. ............. 601/152 |
| 5,591,200 A | | 1/1997 | Cone et al. |
| 5,626,556 A | | 5/1997 | Tobler et al. |
| 6,406,445 B1 | * | 6/2002 | Ben-Nun ..................... 601/152 |

FOREIGN PATENT DOCUMENTS

| | | | |
|---|---|---|---|
| DE | 27 53 523 | 6/1979 | |
| DE | 85 30 876.5 | 2/1986 | |
| DE | 36 39 846 A1 | 2/1988 | |
| EP | 285691 A1 * | 10/1988 | .......... A61H/23/04 |

* cited by examiner

Primary Examiner—Nicholas D. Lucchesi
Assistant Examiner—Quang D. Thanh
(74) Attorney, Agent, or Firm—Browdy and Neimark, P.L.L.C.

(57) ABSTRACT

A compression sleeve is made of a first and a second sheet of a flexible material each having distal and proximal end edges and two lateral edges extending therebetween. The sheets are connected one to the other by a plurality of longitudinal connection lines transverse to the lateral edges. Thus they form a plurality of longitudinal pressure cells each defined between a pair of connection lines and first and second strip regions of the respective first and second sheets. The width of the second strip region between said pair of connection lines is greater than the width of the first strip region. The pressure cells are inflatable and, when inflated to exert pressure on a body, the second strip region of one cell overlaps the second strip region of an immediately adjacent neighboring cell.

11 Claims, 3 Drawing Sheets

COMPRESSION SLEEVE

FIELD OF THE INVENTION

The present invention relates to a compression sleeve designed for applying pressure to a body, particularly, for the purposes of compression therapy.

BACKGROUND OF THE INVENTION

A sleeve of the kind to which the present invention refers has distal and proximal ends and a plurality of annular pressure cells extending parallel to the ends of the sleeve, with inflatable fluid bags disposed in the cells and connectable to an appropriate fluid line. Known sleeves are made in initially flat shape, being adapted to be wrapped around a human body or a limb thereof and fixed thereon. The sleeves are made of two sheets of flexible material such as nylon, that constitute inner and outer layers of the sleeve and have distal and proximal end edges and two lateral edges, and strips of flexible material that extend between the two side edges of the sheets, and are each sewn with its one side on one of the sheets and with its other side either on the other sheet or on an immediately adjacent neighboring strip, whereby the pocket-like cells are formed. The strips are sewn in such a manner that each cell formed thereby, except for the most distal cell, overlaps its immediately adjacent cell to make sure that, when adjacent fluid bags inserted into the cells are inflated, the pressure area defined thereby is continuous. The cells are open adjacent the side edges of the inner and outer sheets to facilitate insertion thereto and withdrawal therefrom of their corresponding inflatable fluid bags.

One example of a sleeve of the kind described above is disclosed in U.S. Pat. No. 5,591,200.

U.S. Pat. No. 5,626,556 discloses another kind of a compression sleeve in which, instead of cells with inflatable fluid bags, longitudinal inflatable pressure chambers are formed by means of connecting inner and outer sheets of the sleeve by a plurality of longitudinal and peripheral sealing lines. The inner and outer sheets in this case are made of fluid-impervious material. However, in this sleeve, immediately adjacent chambers do not overlap and, therefore, when inflated, present a pressure area which has discontinuities along the longitudinal sealing lines.

SUMMARY OF THE INVENTION

The present invention suggests a novel compression sleeve having overlapping inflatable pressure cells.

The sleeve of the present invention has at least a portion thereof made of a first and a second sheet of a flexible material, each having distal and proximal end edges and two lateral edges extending therebetween; the sheets being connected one to the other by a plurality of longitudinal connection lines directed transversely to said lateral edges and thereby forming a plurality of longitudinal pressure cells each defined between a pair of connection lines which form first and second strip regions on the respective first and second sheets, a width of the second strip region between said pair of connection lines, at least in the majority of the cells, being greater than that of the first strip region, said cells being at least indirectly inflatable and, when inflated to exert pressure on a body, having said second strip region of one cell overlapping the second strip region of an immediately adjacent neighboring cell.

Preferably, said first and second sheets are made of a fluid-impervious material, and they are sealingly connected by said longitudinal connection lines and by lateral connection lines extending along said lateral edges, the first or the second strip region of each cell having a fluid opening to enable direct inflation of the cell. This design is simple and easy to manufacture and it may be a cheap solution for disposable sleeves. Alternatively, if desired, the longitudinal connection lines may be in the form of conventional sewn stretches and the cells may be adapted to receive therein fluid bags, such as for example in U.S. Pat. No. 5,591,200.

In a preferred embodiment of the present invention, said second strip region of each cell is formed, along the longitudinal connection lines, with a pleat having a width of about half the difference between the widths of the first and second strip regions. When this difference is about 50%, the width of the pleat and, therefore, the extent of the overlap between two immediately adjacent second strip regions is about 25%. In general, it is preferable that, in the deflated state of the cells, this extent be in the range between 25% to 35%. It is further preferable that the pleats are oriented in the direction towards the proximal end of the sheets.

Preferably, the sleeve further comprises a third sheet of flexible material connected to the first and second sheets along the distal, proximal and lateral edges of these sheets. This third sheet facilitates keeping the second strip regions in their pleated state both when the cells are deflated and inflated. This sheet preferably constitutes an inner layer of the sleeve said first sheet constitutes an outer layer of the sleeve and said second sheet constitutes an intermediate layer of the sleeve.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
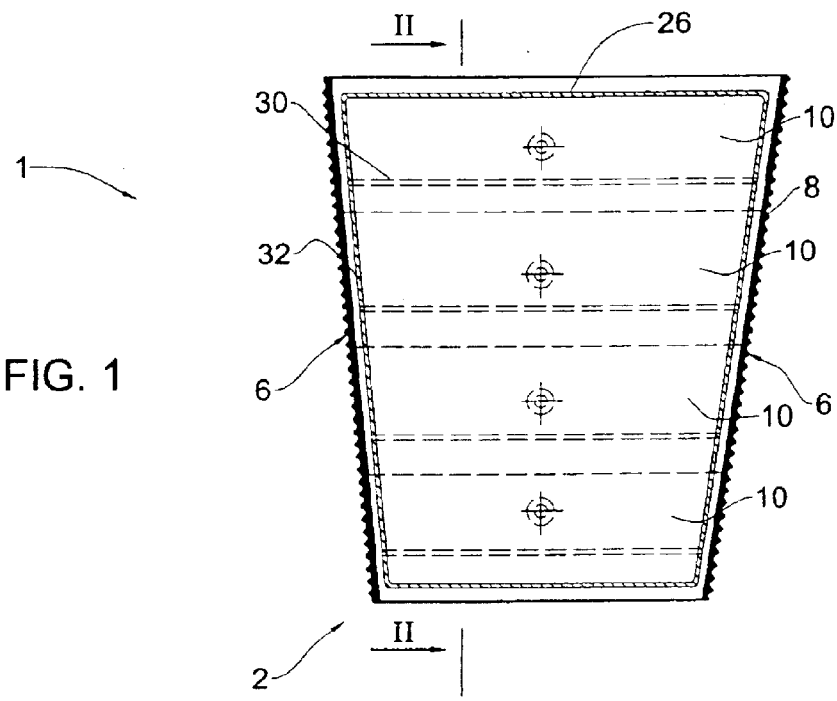
FIG. 1 is a schematic illustration of a compression sleeve of the present invention in a flat and deflated state.
Figure 2:
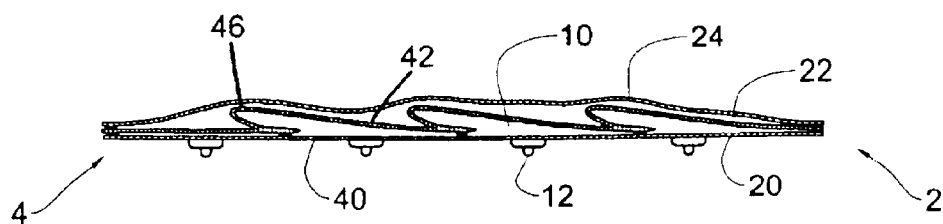
FIG. 2 is a schematic cross-sectional view of the compression sleeve shown in FIG. 1, taken along the line II—II.

FIGS. 1 and 2 show a compression sleeve 1 of the present invention, in a flat state as manufactured. The sleeve is of the kind adapted to be wrapped around a human body or a limb thereof to compress it for the purposes of pressure therapy, in particular to alleviate swelling therein.

Figure 4:
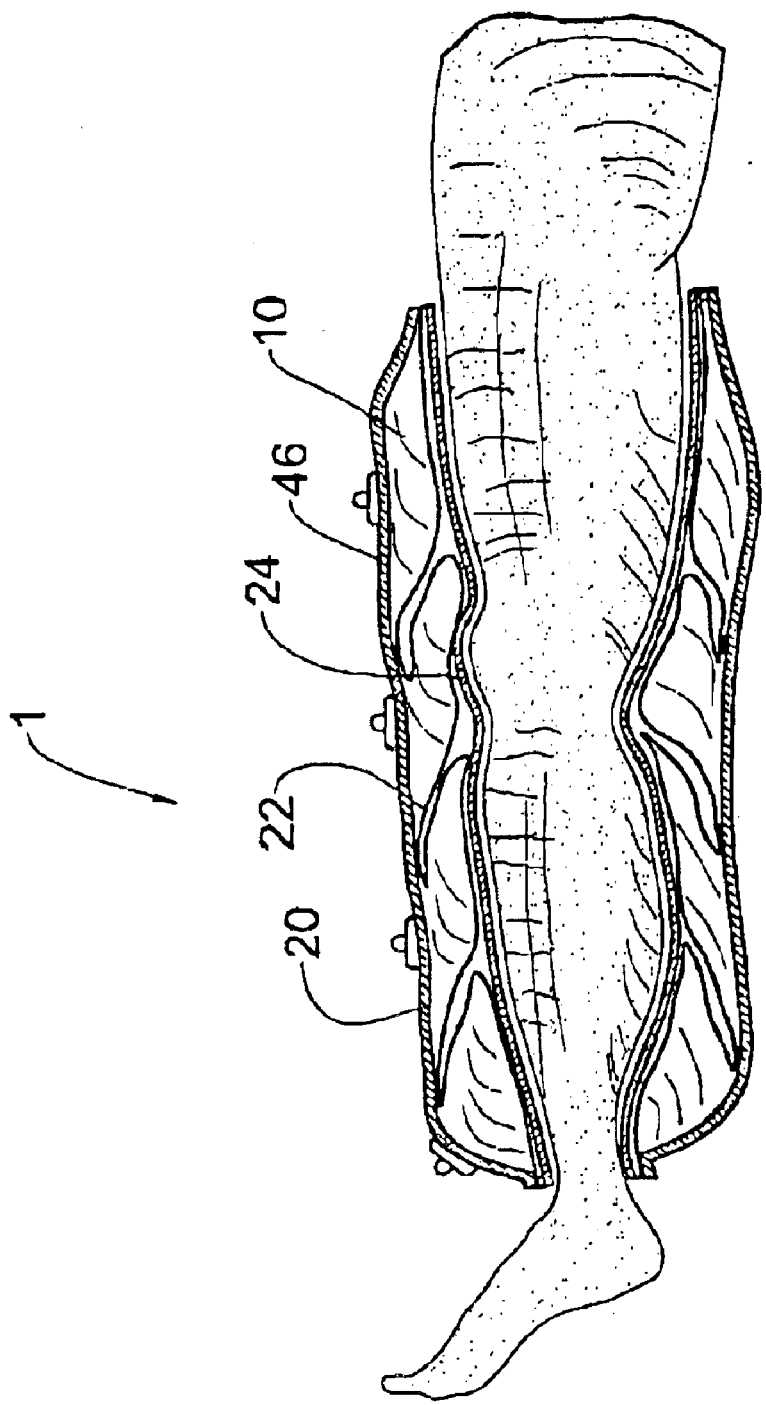
FIG. 4 is a schematic cross-sectional view of a compression sleeve according to the present invention, in use when wrapped around a leg of a patient.

The sleeve 1 is designed for a leg of a patient for use as illustrated in FIG. 4, and as shown in FIG. 1, it has a generally trapezoidal shape with distal and proximal ends 2 and 4, respectively, and sides 6. However, it may have any other shape in accordance with a limb or part of a patient's body to be treated. For the fixation of the sleeve 1 in its operative position, it is provided with fasteners which are shown in FIG. 1 as a zipper 8, but which may be in the form of Velcro fasteners or of any other conventional design.

Figure 3:
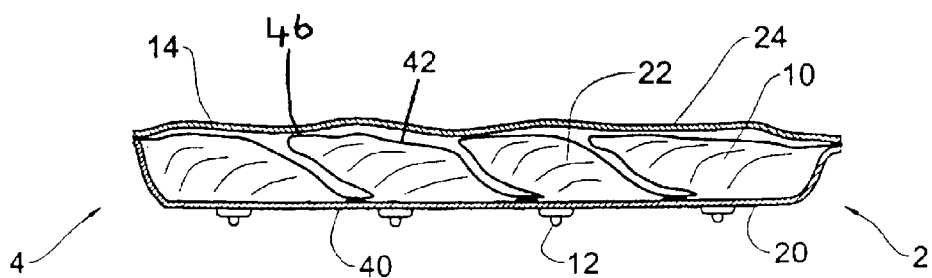
FIG. 3 is a schematic cross-sectional view of the compression sleeve shown in FIG. 2, when inflated.

The sleeve 1 has a plurality of pressure cells 10 having fluid openings 12 to be connected to a fluid line (not shown) for the inflation and deflation of the cells 10 by a fluid 14 to compress a leg of a patient, as shown in FIG. 4, in a controlled manner. The fluid may be in a liquid or gaseous state. In particular, it may be in the form of air. As seen in FIGS. 2, 3 and 4, in both deflated and inflated state, the pressure cells 10 overlap their immediately adjacent neighboring pressure cells in the direction towards the proximal end 4 of the sleeve.

With reference to FIGS. 1 and 2, it will now be explained below how the pressure cells 10 of the sleeve are formed and how it is ensured that they stay in their overlapping state both when inflated and deflated.

As seen in FIGS. 2 and 3, the sleeve 1 is made of first, second and third sheets 20, 22 and 24 of a flexible material, which constitute the sleeve's respective outer, intermediate and inner layers and which are all connected by a peripheral connection line 26 seen in FIG. 1, circumferentially extending along the distal and proximal ends 2 and 4 and sides 6 of the sleeve.

The sheets 20 and 22 are made of a fluid-impervious material, such as for example, nylon coated with polyurethane, and they are sealingly connected with each other by a plurality of longitudinal connection lines 30 directed transversely to the sides 6 of the sleeve 1 and defining therebetween the cells 10. The sheets 20 and 22 are further sealingly connected with each other by lateral connection lines 32 directed along the sides 6 of the sleeve, whereby it is ensured that each cell 10 has fluid-tight boundaries. The sealing connection between the sheets 20 and 22 along the longitudinal and lateral connection lines 30 and 32 may be provided by such means as welding, adhesive bonding or radio frequency treatment, and the like. The longitudinal connection lines 30 that are located adjacent the distal and proximal ends 2 and 4 of the sleeve, and the lateral connection lines 32 that are located adjacent the sides 6 of the sleeve coincide, in the sleeve 1, with the peripheral connection lines 26 seen in FIG. 1, and are made simultaneously therewith. However, this does not necessarily need to be the case.

As best seen in FIGS. 2 and 3, the longitudinal connection lines 30 divide the sheets 20 and 22 into pairs of respective first and second strip regions 40 and 42, Much define therebetween the cells 10. The fluid openings 12 are formed in the first strip regions 40. The second strip regions 42, in all the cells except for the most proximal cell that is disposed adjacent the proximal end 4 of the sleeve, are wider than the first strip regions 40, i.e. the width of tile material of which the second strip regions 42 are made is greater than that of the first strip regions 40. Due to this difference, the second strip regions 42 form pleats 46 which extend along the longitudinal connection lines 30 and are oriented in the direction towards the proximal end 4 of the sleeve. The pleats 46 are formed so as to overlap the second strip regions 42 of immediately adjacent neighboring cells 10, both when the cells 10 are deflated (FIG. 2) and inflated (FIGS. 3 and 4). In the deflated state, the extent of overlap is preferably about 25% to 35%. To fix the strip regions 42 in the pleated state, the lateral connection lines 32 pass through the pleats (not seen). It should be mentioned that in different cells, the widths of the first and second strip regions, as well as the extent of overlap, might be different.

Figure 5A:
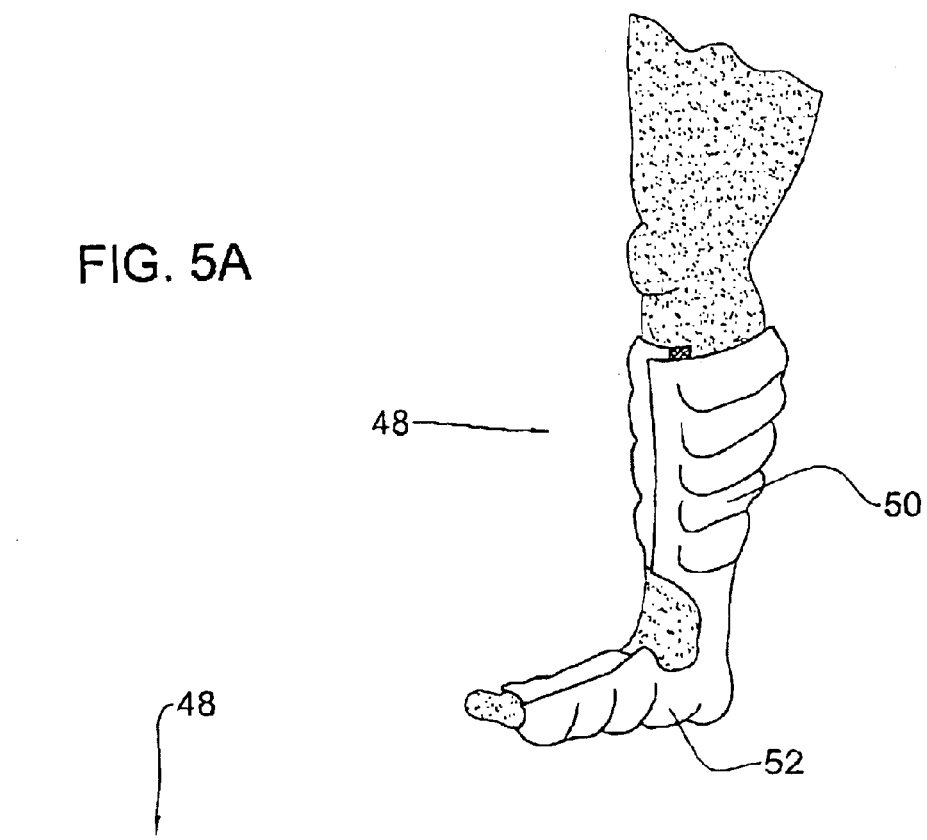
FIGS. 5A and 5B are schematic illustrations of an alternative embodiment of a sleeve according to the present invention, respectively, in use when wrapped around a leg of a patient and in a flat and deflated state.
Figure 5B:
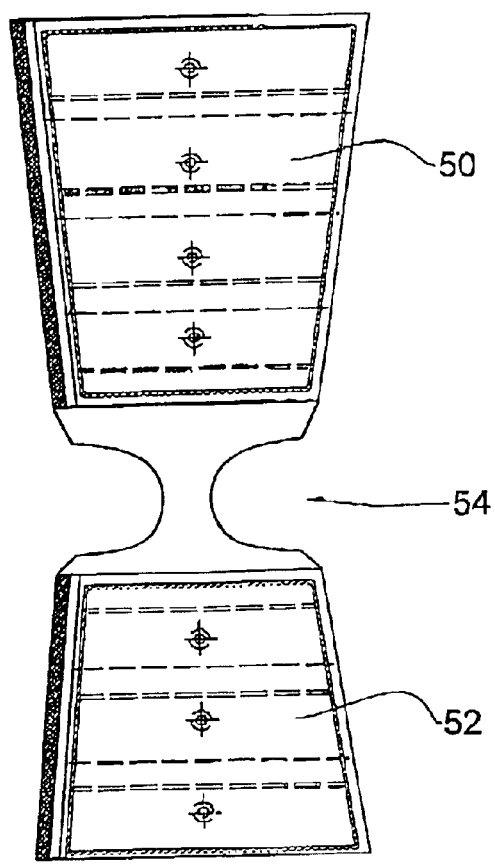

FIGS. 5A and 5B show a different embodiment of a compression sleeve 48 according to the present invention which has a more complex configuration than that of the compression sleeve 1 shown in FIGS. 1 to 4. Namely, the sleeve 48 has two sleeve portions 50 and 52, each of each acts as an individual sleeve having pressure cells designed and, manufactured in the same manner as in the sleeve 1. The sleeve portions 50 and 52 are connected with each other by a non-pressure web 54, which may be made either as a separate piece sewn to the sleeve portions at their associated ends, or as a web cut out in the sleeve portions' common outer sheet. In the latter case, the sleeve portions 50 and 52 each has its individual intermediate and inner sheets attached to their corresponding areas of the common outer sheet disposed on two sides of the web 54.

It should be understood that the above-described embodiments are only examples of a compression sleeve and method of its manufacturing according to the present invention, and that the scope of the present invention fully encompasses other embodiments which may become obvious to those skilled in the art.

What is claimed is:

1. A compression sleeve at least a portion of which is made of a first and a second sheet of a flexible fluid-impervious material, each having distal and proximal end edges and two lateral edges extending therebetween;
   the sheets being sealingly fixed to each other by a plurality of longitudinal connection lines directed transversely to said lateral edges and by lateral connection lines extending along said lateral edges,
   thereby forming a plurality of longitudinal pressure cells each defined between a pair of connection lines, the pair of connecting lines defining first and second strip regions on the respective first and second sheets,
   a width of the second strip region between said pair of connection lines, at least in the majority of the cells, being greater than that of the first strip region,
   to form pleats along the longitudinal connection lines, which are kept in their pleated states by said lateral connection lines, the first or second strip region of each pressure cell having a fluid opening to enable direct inflation of the cell,
   said pressure cells, when inflated to exert pressure on a body, having said second strip region of one cell overlapping the second strip region of an immediately adjacent neighboring cell.

2. A compression sleeve according to claim 1, wherein the width of material of the second strip region is greater than the width of material of the first strip region to about 50% of the width of the first strip region.

3. A compression sleeve according to claim 1, wherein each pleat, when deflated, overlaps the second strip regions of an immediately adjacent neighboring cell to 25% to 35% of the width thereof.

4. A compression sleeve according to claim 1, wherein the pleats are oriented in the direction towards the proximal end edge of the sheets.

5. A compression sleeve according to claim 1, wherein the sleeve further comprises a third sheet of flexible material connected to the first and second sheets along the distal, proximal and lateral edges of these sheets.

6. A compression sleeve according to claim 1, wherein said sleeve further comprising a third sheet for keeping the second sheet regions in their pleated state both when the cells are inflated and deflated, said third sheet constitutes an inner layer of the sleeve, said first sheet constitutes an outer layer of the sleeve and said second sheet constitutes an intermediate layer of the sleeve.

7. A compression sleeve according to claim 1, comprised of at least two sleeve portions having said pressure cells, that are separated by a non-pressure portion.

8. A compression sleeve according to claim 1, adapted to be wrapped around a part of a patient's body or a limb thereof.

9. A compression sleeve at least a portion of which is made of a first and a second sheet of a flexible fluid-impervious material, each having distal and proximal end edges and two lateral edges extending therebetween;

the sheets being sealingly fixed to each other by a plurality of longitudinal connection lines directed transversely to said lateral edges and by lateral connection lines extending along said lateral edges, thereby forming a plurality of longitudinal pressure cells each defined between a pair of connection lines, the pair of connection lines defining first and second strip regions on the respective first and second sheets, a width of the second strip region between said pair of connection lines, at least in the majority of the cells, being greater than that of the first strip region, to form pleats along the longitudinal connection lines, which are kept in their pleated states by said lateral connection lines, the first or second strip region of each pressure cell having a fluid opening to enable direct inflation of the cell, said pressure cells, when inflated to exert pressure on a body, having said second strip region of one cell overlapping the second strip region of an immediately adjacent neighboring cell, said sleeve further comprising a third sheet for keeping the second strip regions in their pleated state when the cells are inflated and deflated.

10. A compression sleeve according to claim 9, wherein said second strip regions of at least the majority of said cells are free of any connection to said third sheet.

11. A compression sleeve according to claim 10, wherein, said third sheet constitutes an inner layer of the sleeve, said first sheet constitutes an outer layer of the sleeve and said second sheet constitutes an intermediate layer of the sleeve.

* * * * *